United States Patent [19]

Ryang

[11] Patent Number: 4,902,750

[45] Date of Patent: Feb. 20, 1990

[54] LATENT CATALYSTS FOR HEAT CURABLE THERMOSETTING RESINS

[75] Inventor: Hong-Son Ryang, Camarillo, Calif.

[73] Assignee: BASF Aktiengesellschaft, Ludwigshafen, Fed. Rep. of Germany

[21] Appl. No.: 320,991

[22] Filed: Mar. 9, 1989

Related U.S. Application Data

[62] Division of Ser. No. 100,651, Sep. 24, 1987, abandoned.

[51] Int. Cl.⁴ .......................... C08F 30/02; C08F 22/40
[52] U.S. Cl. ................................. 525/326.8; 525/340; 526/193; 526/262
[58] Field of Search ................ 526/193, 262; 525/340, 525/326.8; 528/89

[56] References Cited

U.S. PATENT DOCUMENTS 3,843,605  10/1974  Schmidt et al. .

Primary Examiner—Joseph L. Schofer
Assistant Examiner—Jeffrey T. Smith
Attorney, Agent, or Firm—William G. Conger

[57] ABSTRACT

The subject invention relates to N-[3-phosphoranylidenyl-1-azacyclopenta-2,4-dione] radical-containing-compounds which are effective, storage stable latent catalysts for a variety of high performance resin systems.

20 Claims, No Drawings

LATENT CATALYSTS FOR HEAT CURABLE THERMOSETTING RESINS

This is a division of application Ser. No. 100,651, filed Sept. 24, 1987, now abandoned.

BACKGROUND OF THE INVENTION

1. Field of the Invention

The subject invention relates to latent catalysts for heat curable thermosetting resins. More particularly, the subject invention relates to a new class of catalysts which have improved latency at ambient temperatures and which are oxidation and hydrolysis resistant. These catalysts are useful in catalyzing a variety of resin systems, particularly epoxy and bismaleimide resins.

2. Description of the Related Art

Latent catalysts are necessary for the cure of several important categories of resins. The cure of epoxy resins, for example, is generally catalyzed even when "curing agents" such as acid anhydrides or organic diamines are present. Bismaleimide resins may be cured by heat along, but the properties of the cured products are not as good as those achieved when the same resin system is cured catalytically.

Latent catalysts may be divided into two principle groups: those which are activated photochemically, and those which are activated thermally. Photo-activated catalysts are extensively used in the electronics industry in formulating resins useful in processing integrated circuits and circuit boards. In the structural materials area, however, where part sizes are generally much larger and often of complex shape, thermally-activated catalysts are the norm. The discussion which follows relates to this type of latent catalyst.

An ideal latent catalyst will have little or no catalytic activity below a certain threshold temperature, above which the catalyst becomes active. This threshold temperature must be high enough above ambient to facilitate long term storage of the uncured, catalyzed resins and products containing them, but must be low enough to be convenient for the cure of the particular resin system with which the catalyst is used.

When the catalyst has a latency threshold which is too high, several deleterious effects may occur, including thermal decomposition of the resin components; volatilization of low molecular weight resin components or solvents; and extensive thermal curing in conjunction with catalytic cure of the resin. Additionally, subjecting assemblies such as structural composites to wide temperature ranges during processing may cause distortion due to uneven expansion and contraction.

In U.S. Pat. No. 3,562,215, for example, are disclosed substituted urea and guanidine compounds which are used in conjunction with a glycol and with organic lead or mercury derivatives to form a latent catalyst system for epoxy resins. However the catalyst must be used in amounts of approximately ten percent by weight relative to the epoxy resins. Furthermore it is well known that the decomposition of ureas can produce a number of volatile products. Finally, organolead and organomercury compounds are highly poisonous, difficult to handle safely, and may cause environmental problems.

The use of phosphonium halides in conjunction with alkali metal hydroxides or halides are disclosed as latent catalysts for use in epoxy resins in U.S. Pat. No. 4,320,222. However the presence of alkali metal salts may be deleterious to the long term stability of the cured resin. Moreover, the decomposition of the phosphonium halide involves the formation of an organic halide which, in most cases, is relatively volatile. Finally, the phosphonium halides are water soluble and possess strong biocidal properties, thus presenting safety and environmental concerns.

The use of organophosphines and organophosponium salt as latent catalysts for bismaleimide resin systems is disclosed in U.S. Pat. No. 4,644,039. However, organophosphines, particularly the aliphatic phosphines, are volatile compounds of high toxicity and thus also present handling problems. Moreover, many organophosphines, again particularly the aliphatic organophosphines, are readily oxidizable to phosphine oxides which possess little or no catalytic activity. Thus formulation of systems containing these catalysts preferably takes place in inert atmospheres, and subsequent oxidation in situ is possible, causing gradual loss of catalytic activity.

In U.S. Pat. No. 4,131,633 are disclosed latent catalysts prepared by the reaction of maleic anhydride and tris-substituted phosphines. However, the latency threshold of these compounds is rather low, and the products are additionally highly water sensitive, being subject to complete hydrolysis.

It would be desirable to prepare a latent catalyst which is oxidatively and hydrolytically stable under ordinary conditions; which presents a minimum of handling problems; which has a latency threshold which allows for long term storage of uncured products; which is active at a temperature suitable for use with advanced resin systems; and which produces low levels of volatiles upon cure.

SUMMARY OF THE INVENTION

It has now been discovered that catalysts prepared through the reaction of organophosphines with maleimide-group-containing compounds are solids which exhibit excellent storage stabilities with respect to both oxidation and hydrolysis; have latency thresholds which provide for excellent storage stability of catalyzed but uncured resins systems; which produce either no volatiles or very low levels of volatiles upon activation; and which exhibit catalytic activity at temperature suitable for the elevated temperature cure of modern, high strength resin systems. The catalysts are effective in a variety of resin systems, particularly in epoxy resins and bismaleimide resins, and contain the N-[3-phosphoranylidenyl-1-azacyclopenta-2,5-dione] radical having the formula:

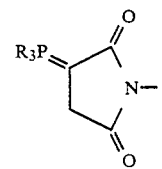

DESCRIPTION OF THE PREFERRED EMBODIMENTS

The latent catalysts of the subject invention are prepared by reacting a tris-substituted organophosphine with a maleimide-group-containing compound. The reaction takes place readily at low temperature, i.e. from about 0° C. to 25° C., preferably in an inert soluent such as dichloromethane.

The tris-substituted phosphines suitable for the preparation of the latent catalysts of the subject invention have the formula $R_3P$, wherein each R may be individually selected from the group consisting of substituted or unsubstituted hydrocarbon groups, in particular alkyl, cycloalkyl, and aryl groups. The term "alkyl group" as used herein and in the claims includes alkyl groups which are substituted by cycloalkyl or aryl groups or by other inert substituents.

Among the many tris-[alkyl] phosphines useful for the practice of the invention are trimethyl-, triethyl-, tris[n-propyl]-, tris[2-propyl]-, tris[n-butyl]-, tris[i-butyl]-, tris [t-butyl]-, tris[n-octyl]-, tris[2-ethylhexyl]-, tridecyl-, tridodecyl-, tribenzyl, and 1,1,1,-tris[2-phenylethyl]phosphines, as well as mixed alkyl phosphines such as methyldiethylphosphine, dibutyloctylphosphine, and the like.

Among the cycloaliphatic phosphines useful are tris-cyclopentyl]-and tris[cyclohexyl]phosphine, tris[2-, and 4-methylcyclohexyl]phosphines, and mixed phosphines such as dibutylcyclohexylphosphine. The cycloaliphatic substituents generally have 5-6 carbons in the ring structure proper.

Among the aryl phosphines which are useful are triphenylphosphine, tris[4-chlorophenyl]phosphine, tritolylphosphine, and mixed phosphines such as cyclohexyldiphenylphosphine and diethylphenylphosphine.

Thus many tris-substituted phosphines are useful. Preferred tris-substituted phosphines, because of their availability and lower cost, are those wherein each R is the same. However mixed phosphines may occasionally be quite useful, as the characteristics of the latent catalysts vary with the nature of the substituents. Most preferred are tributylphosphine and triphenylphosphine.

The maleimide-group-containing compound has the formula

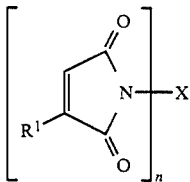

wherein X may be a substituted or unsubstituted hydrocarbon group having a valence, n, of from 1 to about 4, and a formula $CY_3$, wherein Y may be hydrogen, an alkyl, cycloalkyl, or aromatic group which is optionally substituted with a maleimide group having the formula

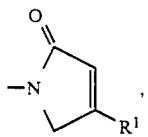

or wherein Y may represent a polyoxyalkylene group such as polyoxyethylene, polyoxypropylene, or polyoxybutylene, or other suitable organic group such as those described in the text which follows, and wherein $R^1$ is hydrogen, substituted or unsubstituted alkyl, cycloaklyl, or aryl, but preferably hydrogen.

The maleimide-group-containing compounds useful in preparing latent catalysts are themselves generally prepared by reacting the corresponding amine with maleic anhydride. The synthesis of such maleimides is well known to those skilled in the art. Suitable maleimides are, for example, the maleimides of aromatic amines such as aniline; o-,m-,and p-toluidine; 2,4-and 2,6-toluene diamines; aromatic diamines having the formula

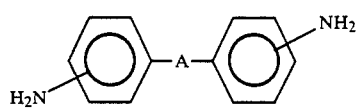

wherein A may be

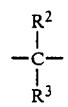

wherein $R^2$ and $R^3$ may be hydrogen, $C_1-C_6$ lower alkyl, or aryl;

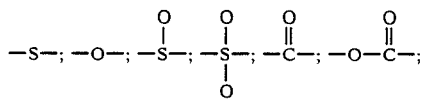

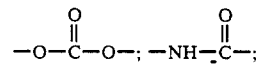

alkylene; oxyalkylene, and polyoxyalkylene; aromatic polyamines, particularly those prepared through the condensation of aniline or substituted anilines with formaldehyde (e.g. polymeric MDA); aliphatic amines such as the various $C_1-C_{20}$ alkyl monoamines; the alkylene diamines, particularly ethylenediamine; the polyalkylene polyamines such as diethylenetriamine and amine terminated polyoxyalkylene polyethers. Cycloalklamines such as 1,4-cyclohexanediamine and 1,4-bis[aminomethyl]cyclohexane are also useful.

The maleimide-group-containing compounds may also be substituted with other organic groups such as hydroxyl, halo, acyloxy, carbonamide, alkoxy, and cyano groups. The maleimide of p-aminophenol is an example of such a compound. Additional maleimides are those of amines having the following structures:

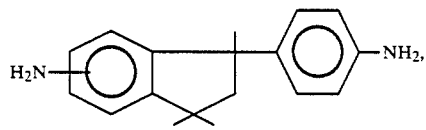

and

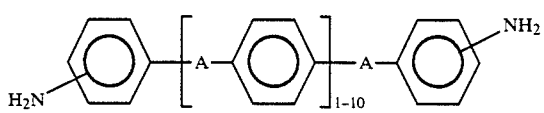

particularly preferred are the maleimides of 1,4-phenylenediamine, p-aminophenol, 4,4'-diaminodiphenylmethane, and 4,4'-diaminodiphenylsulfone. As can be seen, the bismaleimides which may work in the present invention are exceptionally numerous and varied. As the properties of the latent catalysts depend upon the nature of both the phosphine and the maleimide, the latent catalysts of the subject invention may be varied to suit many applications.

The latent catalysts of at the subject invention are especially useful in epoxy systems, particularly those containing phenolic or carboxylic anhydride curing agents. The latent catalysts also find use in maleimide systems, especially those containing alkenylphenols as comonomers.

In preparing the catalyzed resins, the necessary quantity of catalyst, which is generally from about 0.01 percent to about 5 percent by weight based upon the curable resin components, more preferably from about 0.5 percent to 4 percent by weight, and most preferably about 1-3 percent by weight, is mixed with the resin components to form a homogenous mixture. Mixing generally takes place at a modestly elevated temperature, for example from 70° C. to 120° C., preferably from about 80° C. to about 100° C. If a curing agent is used, as is generally the case with epoxy resins, the catalyzed resin absent the curing agent is generally allowed to cool somewhat, for example to about 70° C. before the curing agent is added.

The catalysts of the subject invention are generally useful whenever a phosphine or phosphonium salt catalyst would be effective. In addition to epoxy resin compositions and maleimide resin compositions, these include resins whose reactive monomers may be cyanates, isocyanates, acrylates, and alkenyl and alkynyl resins. This list is not exhaustive. In the claims which follow the example, the term "heat-curable resin" should be taken to mean any resin system the thermal cure of which can be accelerated through the use of the latent catalysts of the subject invention.

To evaluate a resin system with respect to its catalysis with the latent catalysts of the subject invention, a simple test is to prepare a resin system both with and without from about 1-5 percent by weight of the latent catalyst. The gel times of the catalyzed and non-catalyzed systems are then compared at a temperature sufficient to activate the catalyst. If the latent catalyst is effective in causing a decrease in gel time of the resin system, then the heat-curable resin is one which is within the scope of the claims.

The examples which follow illustrates the preparation of several catalysts and their use in catalyzing a variety of heat-curable, thermosetting resins. The examples are not limiting, but are illustrative only.

EXAMPLE 1

Reaction of Triphenylphosphine with the Bismaleimide of 4,4'-Diaminodiphenylmethane.

The bismaleimide (7.16, 0.02 mole) is dissolved in CH$_2$Cl$_2$ (30 ml) in a 250 ml glass reactor cooled by means of an ice-water bath. To the solution, triphenylphosphine (11.0 g, 0.042 mole) in 20 ml CH$_2$Cl$_2$ is slowly added under N$_2$ flow while stirring. The resulting red solution is stirred overnight at room temperature. Addition of ethyl acetate gives an orange precipitate which is separated by filtration, washed with cold ethylacetate, and dried under vacuum.

Yield of catalyst (m.p. >200° C.) was 15.3 g. Analytical results are consistent with a compound corresponding to the structure Ia.

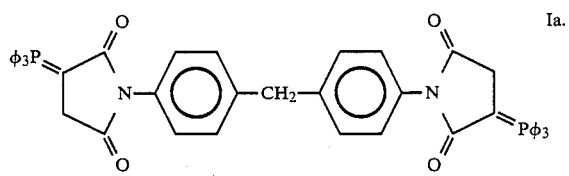

EXAMPLE 2

Reaction of Tributylphosphine with the Bismaleimide of 4,4'-Diaminodiphenylmethane Tributylphosphine (8.50 g, 0.042 mole) and CH$_2$Cl$_2$ (50 ml) are charged to a 250 ml glass reactor under N$_2$ flow then cooled with an ice-water bath. To the solution, the bismaleimide (7.16 g, 0.02 mole) in CH$_2$Cl$_2$ (50 ml) is slowly added while stirring. The resulting red solution is stirred at room temperature overnight. Addition of ethyl acetate causes the precipitation of the product which is separated by filtration and washed with cold ethyl acetate. Drying under vacuum gives 14.0 g of orange solid (m.p. >200° C.). Analytical results are consistent with a compound corresponding to the structure Ib.

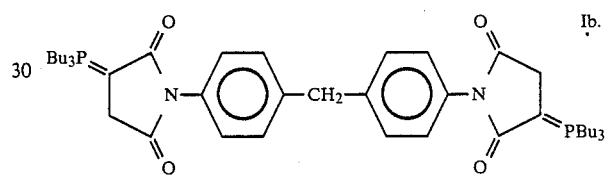

EXAMPLE 3

Reaction of Triphenylphosphine with the Maleimide of p-aminophenol.

A mixture of the maleimide (4.73 g, 0.025 mole) and 50 ml of CH$_2$Cl$_2$ is slowly added to a solution of triphenylphosphine (6.80 g, 0.026 mole) in 50 ml of CH$_2$Cl$_2$ at 15° C. under N$_2$ while stirring. The resulting mixture is stirred overnight at room temperature. Filtration, followed by washing with cold ethyl acetate gives a colorless solid (yield 11.0 g, m.p. 180° C. with decomposition). Analytical results are consistent with a compound corresponding to the structure II.

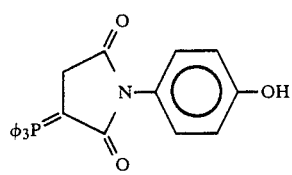

EXAMPLES 4-7

Heat-Cure of Bismaleimide Resins

Heat-Curable Bismaleimide resin systems are prepared in the following manner:

The bismaleimide of 4,4'-diaminodiphenylmethane (6.7g) and o,o'-diallylbisphenol A (3.3g) are stirred at 140° C. to give a uniform mixture. The mixture is cooled to 80° C. and catalyst (0.05g) is added while stirring. Gel times are measure din aliquots of each of the catalyzed mixtures at both 177° C. and 120° C. Results are shown in Table I.

TABLE I

| Example | Latent Catalyst of | Gel Time (Minutes) at 177° C. | 120° C. |
|---|---|---|---|
| 4 | Example 1 | 10 | 60 |
| 5 | Example 2 | 10 | — |
| 6 | Example 3 | 10 | 80 |
| 7 | No Catalyst | 23 | — |

Uncured, catalyzed samples are allowed to stand at room temperature for four weeks. No loss of tack is observed.

EXAMPLE 8

Preparation of Precatalyzed Epoxy Resins

Precatalyzed epoxy resins are prepared by mixing a diglycidylether of bisphenol A (DER 332 ® available from the Dow Chemical Co., Midland, MI., epoxy equivalent weight=172, 10.00 g) and the catalysts (0.88 g) from Examples 1-3, at 80° C. The mixtures are stored at room temperature for four weeks. No change in EEW is observed, illustrating the storage stability of the catalyzed systems.

EXAMPLE 9

Preparation of Linear Epoxy Resins

A 100 ml glass reactor equipped with a mechanical stirrer is charged with the diglylcidyl ether of bisphenol A (DER 332 ®, EEW 172, 15.2 g), bisphenol A (4.8 g), and the catalyst (0.09 g) from Example 1 dissolved in DER ® (1.0 g). The stirred reaction mixture is heated to 150° C. for 10 hours to yield a viscous oil which solidified at room temperature. EEW of the resulting mixture is 444 (theoretical EEW=406). Further mixing at 150° C. does not alter the EEW value.

EXAMPLES 10-13

Samples are prepared in the following manner: An expoxy novolac (DEN ® 438, available from the Dow Chemical Co., Midland, MI., EEW=176, 38.0 g) and bisphenol A (12.0 g) are mixed at 100° C. to give a clear mixture. At 70° C., the above mixture (10.0 g) and the precatalyzed epoxy (1.09 g) from Example 8 are mixed in an aluminum dish to give a uniform mixture. Gel times are measured in aliquots of each of the catalyzed mixtures at both 177° C. and 120° C. Results are shown in Table II. A sample (Example 12) was also prepared from DEN 438 (17.6 g), bisphenol A (3.4 g), and triphenylphosphine (0.052 g).

TABLE II

| Example | Latent Catalyst of | Gel Time (Minutes) at 177° C. | 120° C. |
|---|---|---|---|
| 10 | Example 1 | 4.0 | 40 |
| 11 | Example 3 | 1.5 | 12 |
| 12 | Triphenylphosphine | 1.3 | 9 |
| 13 | No Catalyst | >60 | — |

Uncured samples are allowed to stand at room temperature. The triphenylphosphine catalyzed sample (Example 12) shows the loss of tack after three days, whereas the samples from Example 10, 11, and 13 show no loss of tack even after two weeks.

EXAMPLE 14

Heat-Cure of Epoxy Resin

Nadic anhydride (4.0 g) is dissolved in a novolac epoxy (DEN ® 438, 5.0 g) at 100° C. At 70° C., the catalyst (0.5 g) from Example 3 dissolved in DER 332 (0.5 g) is added while stirring.

The resulting resin system is cured at 120° C. Gel time is 21 minutes.

The embodiments of the invention in which an exclusive privilege or property is claimed are defined as follows:

1. A heat-curable resin system, comprising:
   (a) a bismaleimide resin; and
   (b) an effective amount of a catalyst which promotes thermal curing of said bismaleimide resin, wherein said catalyst contains at least one N-[3-phosphoranylidenly-1-azacyclopenta-2,4-dione] radical, and having the formula:

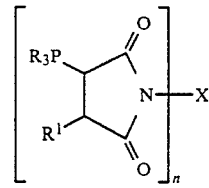

wherein $R^1$ and each R are individually selected from the group consisting of substituted and unsubstituted alkyl, cycloalkyl, and aryl radicals; and wherein X is an organic radical of valence n wherein n is a whole number from 1 to about 4.

2. The resin system of claim 1 wherein said organic radical X is an aryl radical.

3. The compound of claim 1 wherein said compound contains two N-[3-phosphoranylidenyl-1-azacyclopenta-2,4-dione] radicals.

4. The compound of claim 3 wherein said N-[3-phosphoranylidenyl-1-azacyclopenta-2,4-dione] radicals are bridged by a connecting group X selected from the group consisting of alkylene, cycloalkylene, arylene, and polyoxyalkylene radicals.

5. The compound of claim 1 wherein each R is individually selected from the group consisting of $C_1$–$C_{10}$ alkyl, $C_5$–$C_7$ cycloalkyl, and $C_6$–$C_{10}$ aryl groups.

6. A heat-curable resin system, comprising:
   (a) a bismaleimide resin; and
   (b) an effective amount of a catalyst which promotes thermal curing of said bismaleimide resin, wherein said catalyst contains at least a compound having the formula

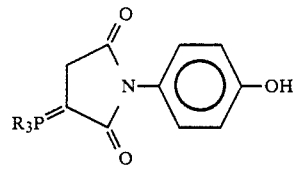

wherein each R is individually selected from the group consisting of $C_1$–$C_{10}$ lower alkyl, $C_5$–$C_7$ cycloalkyl, and $C_6$–$C_{10}$ aryl.

7. A heat-curable resin system, comprising:
   (a) bismaleimide resin; and (b) an effective amount of a catalyst which promotes thermal curing of said bismaleimide resin, wherein said catalyst contains at least one compound having the formula

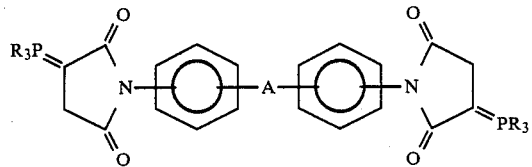

wherein each R is individually selected from the group consisting of $C_1$–$C_{10}$ lower alkyl, $C_5$–$C_7$ cycloalkyl, and $C_6$–$C_{10}$ aryl; and wherein A is selected from the group consisting

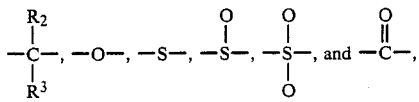

and wherein $R^2$ and $R_3$ are individually hydrogen, $C_1$–$C_6$ lower alkyl, or phenyl.

8. The resin system of claim 1 further comprising:
(c) an alkenylphenol coreactant.
9. The resin system of claim 2, further comprising:
(c) an alkenylphenol coreactant.
10. The resin system of claim 3 further comprising:
(c) an alkenylphenol coreactant.
11. The resin system of claim 4 further comprising:
(c) an alkenylphenol coreactant.
12. The resin system of claim 5, further comprising:
(c) an alkenylphenol coreactant.
13. The resin system of claim 6, further comprising:
(c) an alkenylphenol coreactant.
14. The resin system of claim 7 further comprising:
(c) an alkenylphenol coreactant.
15. The resin system of claim 8 wherein said alkenyl radical is selected from the group consisting of propenyl, isopropenyl, vinyl, allyl, and methallyl radicals.
16. The resin system of claim 13 wherein said alkenyl radical is selected from the group consisting of propenyl, isopropenyl, vinyl, allyl, and methallyl radicals.
17. The resin system of claim 14 wherein said alkenyl radical is selected from the group consisting of propenyl, isopropenyl, vinyl, allyl, and methallyl radicals.
18. The resin system of claim 8 wherein said alkenylphenol is selected from the group consisting of o,o'-diallylbisphenol A and o,o'-dipropenylbisphenol A.
19. The resin system of claim 13 wherein said alkenylphenol is selected from the group consisting of o,o'-diallylbisphenol A and o,o'-dipropenylbisphenol A.
20. The resin system of claim 14 wherein said alkenylphenol is selected from the group consisting of o,o'-diallylbisphenol A and o,o'-dipropenylbisphenol A.

* * * * *